(12) United States Patent
Chen et al.

(10) Patent No.: US 10,278,796 B2
(45) Date of Patent: *May 7, 2019

(54) ORAL CARE GEL DISPENSER SYSTEMS

(75) Inventors: Elva Chen, New Brunswick, NJ (US); Sharon Kennedy, Randallstown, MD (US); Yelloji-Rao Mirajkar, Piscataway, NY (US); Suzanne Jogun, Wayne, NJ (US); Michael Prencipe, Princeton Junction, NJ (US)

(73) Assignee: Colgate-Palmolive Company, New York, NY (US)

( * ) Notice: Subject to any disclaimer, the term of this patent is extended or adjusted under 35 U.S.C. 154(b) by 1150 days.

This patent is subject to a terminal disclaimer.

(21) Appl. No.: 14/356,810

(22) PCT Filed: Nov. 15, 2011

(86) PCT No.: PCT/US2011/060678
§ 371 (c)(1),
(2), (4) Date: May 7, 2014

(87) PCT Pub. No.: WO2013/074080
PCT Pub. Date: May 23, 2013

(65) Prior Publication Data
US 2014/0322666 A1 Oct. 30, 2014

(51) Int. Cl.
| | | |
|---|---|---|
| A61C 19/06 | (2006.01) | |
| A61K 8/73 | (2006.01) | |
| A61K 8/04 | (2006.01) | |
| A61Q 11/00 | (2006.01) | |
| A46B 11/00 | (2006.01) | |
| A61C 17/02 | (2006.01) | |
| A61K 49/00 | (2006.01) | |

(52) U.S. Cl.
CPC ........ *A61C 19/066* (2013.01); *A46B 11/0055* (2013.01); *A61C 17/0202* (2013.01); *A61C 17/0217* (2013.01); *A61K 8/042* (2013.01); *A61K 8/73* (2013.01); *A61K 8/731* (2013.01); *A61K 49/0073* (2013.01); *A61Q 11/00* (2013.01); *A46B 2200/1066* (2013.01); *A61K 2800/45* (2013.01); *A61K 2800/872* (2013.01)

(58) Field of Classification Search
None
See application file for complete search history.

(56) References Cited

U.S. PATENT DOCUMENTS

| | | | | |
|---|---|---|---|---|
| 3,903,252 A | * | 9/1975 | Stearns | A61K 8/466 424/49 |
| 4,348,378 A | | 9/1982 | Kosti | |
| 4,459,277 A | | 7/1984 | Kost | |
| 4,483,782 A | | 11/1984 | Cox et al. | |
| 4,992,256 A | * | 2/1991 | Skaggs | A61K 8/466 424/440 |
| 5,098,691 A | | 3/1992 | Simone et al. | |
| 6,238,648 B1 | | 5/2001 | Leusch et al. | |
| 6,488,945 B2 | | 12/2002 | Sato | |
| 2003/0118522 A1 | | 6/2003 | Leinen et al. | |
| 2007/0009447 A1 | * | 1/2007 | Gadkari | A61K 8/19 424/49 |
| 2008/0166307 A1 | | 7/2008 | Fontana et al. | |
| 2008/0253975 A1 | | 10/2008 | Walsh et al. | |
| 2011/0225759 A1 | | 9/2011 | Fleuren | |
| 2012/0034016 A1 | * | 2/2012 | Jimenez | A46B 11/0024 401/174 |
| 2014/0287380 A1 | | 9/2014 | Chen et al. | |

FOREIGN PATENT DOCUMENTS

| | | |
|---|---|---|
| DE | 2415093 | 10/1974 |
| FR | 2463613 | 2/1981 |
| JP | 2000136119 | 5/2000 |
| JP | 2009096770 | 5/2009 |
| WO | WO 99/38482 | 8/1999 |
| WO | WO 2003000215 | 1/2003 |
| WO | WO 04/032674 | 4/2004 |
| WO | WO 2005058185 | 6/2005 |
| WO | WO 2009/087626 | 7/2009 |
| WO | WO 2010/047576 | 4/2010 |
| WO | WO 2011/078863 | 6/2011 |
| WO | WO 2011/078864 | 6/2011 |
| WO | WO 2011/079025 | 6/2011 |
| WO | WO 2011/079028 | 6/2011 |

OTHER PUBLICATIONS

International Search Report and the Written Opinion issued in International Application PCT/US2011/60676 dated Sep. 25, 2012. WO.
Written Opinion of the International Preliminary Examining Authority issued in International Application PCT/US2011/60678 dated Dec. 12, 2013. WO.

* cited by examiner

*Primary Examiner* — Lezah Roberts

(57) ABSTRACT

The invention provides an oral care system comprising a gel in a pen dispenser, the dispenser comprising a chamber which permits dispensing of a measured amount of the gel, wherein the gel exhibits a Herschel-Bulkley yield stress of 10 to 230 dynes/cm2, a Herschel-Bulkley viscosity of 3 to 500 poise, and a Herschel-Bulkley rate index of 0.4 to 0.6, the specific viscosity permitting efficient application of the gel, as well as methods of using the same.

18 Claims, No Drawings

1

ORAL CARE GEL DISPENSER SYSTEMS

FIELD OF THE INVENTION

The present invention relates to oral care systems comprising pen dispensers and gels, e.g., plaque indicator gels and plaque removal gels.

BACKGROUND OF THE INVENTION

Applying oral care products to teeth can present difficulties. For example, oral care compositions comprising dyes that reveal plaque have been known for many years and include liquids, tablets, rinses, sprays, lozenges, and dentifrice materials. Application of these compositions can be messy, as the dye is capable of coloring not only the plaque but also the lips, gums, tongue, mouth area, towels and countertops. In other instances, it may be desirable to apply oral care products such as bleaches or other antibacterial materials in a precise way.

There is an unmet market need for a product that apply oral care products to the teeth, without messiness or difficulty of use and application.

BRIEF SUMMARY OF THE INVENTION

Following extensive formulation development and consumer testing, we have developed gels suitable for application to the teeth with a pen-type device, having a viscosity which permits controlled application and retention on the teeth for a sufficient period to allow the plaque to absorb the dye or other active agent, and further permits the gel to be dispensed easily and spread evenly on the teeth. Identifying the correct viscosity for use with the dispenser system presented significant challenges because the gels must have suitable rheological properties when dispensed, when spread on the teeth, and following application. The desired rheology at each of these points is different.

Characterization and optimization of the viscosity of such non-Newtonian fluids is complex. The Herschel-Bulkley (HB) model is a generalized model of a non-Newtonian fluid, in which the strain experienced by the fluid is related to the stress in a non-linear way. Three parameters characterize this relationship: the consistency k, the flow index n, and the yield shear stress $\tau_0$. The consistency is a simple constant of proportionality. The flow index measures the degree to which the fluid is shear-thinning or shear-thickening. Finally, the yield stress quantifies the amount of stress that the fluid may experience before it yields and begins to flow.

The gels for use in the invention are shear-thinning, meaning that the viscosity of the gel decreases in accordance with the Herschel-Bulkley Model as more force is applied (shear stress). The Herschel-Bulkley Model provides a profile of the rheology of the gels at different shear stress. Through empirical evaluation of a number of gels, it is determined that the gels in accordance with the invention should exhibit a Herschel-Bulkley yield stress of 10 to 230 dynes/cm$^2$, e.g., 30 to 45 dynes/cm$^2$, a Herschel-Bulkley viscosity of 3 to 500 poise, e.g., 30 to 45 poise, and a Herschel-Bulkley rate index of 0.4 to 0.6, e.g. 0.5 to 0.6.

The oral care systems of the invention thus comprise a gel in a pen dispenser, the dispenser comprising a chamber which permits dispensing of a measured amount of the gel to an applicator head, e.g. a doe foot or brush applicator head, wherein the gel exhibits a Herschel-Bulkley yield stress of 10 to 230 dynes/cm$^2$, e.g., 30 to 45 dynes/cm$^2$, a Herschel-Bulkley viscosity of 3 to 500 poise, e.g., 30 to 45 poise, and a Herschel-Bulkley rate index of 0.4 to 0.6, e.g. 0.5 to 0.6.

Using a gel having a specific viscosity in a pen applicator device allows for more controlled application and reduces the level of dye required in the formulation, thereby making the application more efficient, more effective, and less messy than prior art approaches.

Further areas of applicability of the present invention, including methods of making and using the gels for use in the invention, will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

The following description of the preferred embodiment(s) is merely exemplary in nature and is in no way intended to limit the invention, its application, or uses.

In one embodiment, the gel in the dispenser is an orally acceptable plaque indicator gel (Gel 1) comprising a dye in sufficient concentration to visibly stain plaque upon application, the gel having a Herschel-Bulkley yield stress of 10 to 230 dynes/cm$^2$, e.g., 30 to 45 dynes/cm$^2$, a Herschel-Bulkley viscosity of 3 to 500 poise, e.g., 30 to 45 poise, and a Herschel-Bulkley rate index of 0.4 to 0.6, e.g. 0.5 to 0.6. For example, the invention provides in various embodiments 1.1. Gel 1 wherein the elastic modulus (G') is 25 to 1750 dyne/cm$^2$, e.g., 250 to 400 dyne/cm$^2$;

1.2. Gel 1 or 1.1 wherein the viscous modulus (G") is 20 to 750 dyne/cm$^2$, e.g., 120 to 180 dyne/cm$^2$;

1.3. Any of the foregoing gels wherein the critical stress is 2.5 to 15 dyne/cm$^2$, e.g, 4 to 6 dyne/cm$^2$;

1.4. Any of the foregoing gels wherein the ratio of the elastic modulus to the viscous modulus (G'/G") is 1-3, e.g., 1.5 to 2.3, e.g., about 2;

1.5. Any of the foregoing gels comprising a thickening agent selected from carboxyvinyl polymers, carrageenan, hydroxyethyl cellulose, laponite, water soluble salts of cellulose ethers such as sodium carboxymethylcellulose and sodium carboxymethyl hydroxyethyl cellulose, natural gums such as gum karaya, xanthan gum, gum arabic, and gum tragacanth and combinations thereof.

1.6. Any of the foregoing gels comprising a thickening agent selected from homopolymers of acrylic acid crosslinked with an alkyl ether of pentaerythritol or an alkyl ether of sucrose, and carbomers.

1.7. Any of the foregoing gels comprising a thickening agent selected from copolymers of lactide and glycolide monomers, the copolymer having the molecular weight in the range of from about 1,000 to about 120,000 (number average).

1.8. Any of the foregoing gels comprising a thickener selected from cellulose derivatives (for example carboxymethyl cellulose), polysaccharide gums (for example xanthan gum or carrageenan gum), and combinations thereof.

1.9. Any of the foregoing gels comprising 0.2-1.5% xanthan gum and 0.2-3% carboxymethyl cellulose;

1.10. Any of the foregoing gels comprising 30-50% humectants selected from glycerin, sorbitol, xylitol, and combinations thereof;

1.11. Any of the foregoing gels comprising the following ingredients by weight percent:

| Water | 50-60% |
|---|---|
| Xanthan gum | 0.2-1.5%, e.g., about 0.5% |
| Sodium carboxymethylcellulose (CMC) | 0.2-3%, e.g, 1-2%, e.g., about 1.2% |
| Sorbitol (70% aqueous solution) | 15-25%, e.g., about 20% |
| Glycerin | 15-25%, e.g., about 20% |
| Dye | 0.01-0.1%, e.g., about 0.05% |

1.12. Any of the foregoing gels comprising flavorings, e.g. saccharin, mint flavor, and combinations thereof;
1.13. Any of the foregoing gels comprising a surfactant, e.g., sodium lauryl sulfate, e.g., 1-2%;
1.14. Any of the foregoing gels comprising a fluoride ion source, e.g. sodium fluoride, e.g., 0.075-0.15%, e.g., about 0.11%;
1.15. Any of the foregoing gels wherein the dye is selected from FD&C Red No. 3, FD&C Blue No. 1, FD&C Violet No. 1, FD&C Green No. 1, FD&C Green No. 2, FD&C Green No. 3, and mixtures thereof;
1.16. Any of the foregoing gels wherein the dye is FD&C Green No. 3;
1.17. Any of the foregoing gels where the amount of dye is less than 0.1%, e.g., 0.01-0.1%, e.g., about 0.05% by weight of the total formulation.

In a further embodiment, the gel in the dispenser is a plaque removal gel, for example, an orally acceptable plaque removal gel (Gel 2) comprising antiplaque agent in sufficient concentration to kill bacteria and/or remove plaque upon application, the gel having a Herschel-Bulkley yield stress of 10 to 230 dynes/cm$^2$, e.g., 30 to 45 dynes/cm$^2$, a Herschel-Bulkley viscosity of 3 to 500 poise, e.g., 30 to 45 poise, and a Herschel-Bulkley rate index of 0.4 to 0.6, e.g. 0.5 to 0.6. For example, the invention provides in various embodiments 2.0. Gel 2 wherein the elastic modulus (G') is 25 to 1750 dyne/cm$^2$, e.g., 250 to 400 dyne/cm2;
2.1. Gel 2 or 2.0 wherein the viscous modulus (G") is 20 to 750 dyne/cm$^2$, e.g., 120 to 180 dyne/cm$^2$;
2.2. Any of the foregoing gels wherein the critical stress is 2.5 to 15 dyne/cm$^2$, e.g, 4 to 6 dyne/cm$^2$;
2.3. Any of the foregoing gels wherein the ratio of the elastic modulus to the viscous modulus (G'/G") is 1-3, e.g., 1.5 to 2.3, e.g., about 2;
2.4. Any of the foregoing plaque removal gels comprising a thickening agent selected from carboxyvinyl polymers, carrageenan, hydroxyethyl cellulose, laponite, water soluble salts of cellulose ethers such as sodium carboxymethylcellulose and sodium carboxymethyl hydroxyethyl cellulose, natural gums such as gum karaya, xanthan gum, gum arabic, and gum tragacanth and combinations thereof;
2.5. Any of the foregoing plaque removal gels comprising a thickening agent selected from homopolymers of acrylic acid crosslinked with an alkyl ether of pentaerythritol or an alkyl ether of sucrose, and carbomers;
2.6. Any of the foregoing plaque removal gels comprising a thickening agent selected from copolymers of lactide and glycolide monomers, the copolymer having the molecular weight in the range of from about 1,000 to about 120,000 (number average);
2.7. Any of the foregoing plaque removal gels comprising a thickener selected from cellulose derivatives (for example carboxymethyl cellulose), polysaccharide gums (for example xanthan gum or carrageenan gum), and combinations thereof.
2.8. Any of the foregoing plaque removal gels comprising 0.2-1.5% xanthan gum and 0.2-3% carboxymethyl cellulose;
2.9. Any of the foregoing plaque removal gels comprising 30-50% humectants selected from glycerin, sorbitol, xylitol, and combinations thereof;
2.10. Any of the foregoing plaque removal gels comprising the following ingredients by weight percent:

| Water | 50-60% |
|---|---|
| Xanthan gum | 0.2-1.5%, e.g., about 0.5% |
| Sodium carboxymethylcellulose (CMC) | 0.2-3%, e.g, 1-2%, e.g., about 1.2% |
| Sorbitol (70% aqueous solution) | 15-25%, e.g., about 20% |
| Glycerin | 15-25%, e.g., about 20% |
| Antiplaque agent | 0.01-10%, e.g., about 1-5% |

2.11. Any of the foregoing plaque removal gels comprising flavorings, e.g. saccharin, mint flavor, and combinations thereof;
2.12. Any of the foregoing plaque removal gels comprising a surfactant, e.g., sodium lauryl sulfate, e.g., 1-2%;
2.13. Any of the foregoing plaque removal gels comprising a fluoride ion source, e.g. sodium fluoride, e.g., 0.075-0.15%, e.g., about 0.11%;
2.14. Any of the foregoing plaque removal gels wherein the antiplaque agent comprises an antibacterial agent, e.g., selected from an antibacterial agent selected from triclosan, herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, seabuckthorn extract, propolis), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, antibacterial metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing.
2.15. Any of the foregoing plaque removal gels wherein the antiplaque agent comprises triclosan;
2.16. Any of the foregoing plaque removal gels wherein the antiplaque agent comprises a bleach or whitening agent, e.g., selected from a whitening agent selected from a whitening active selected from the group consisting of peroxides, hydrogen peroxide polymer completexes, e.g., polyvinylpyrrolidone peroxide complexes, urea peroxide, metal chlorites, perborates, percarbonates, peroxyacids, hypochlorites, and combinations thereof;

2.17. Any of the foregoing plaque removal gels wherein the antiplaque agent comprises cetylpyridinium chloride;

2.18. Any of the foregoing plaque removal gels further comprising one or more synthetic anionic polymeric polycarboxylates, e.g., selected from 1:4 to 4:1 copolymers of maleic anhydride or acid with another polymerizable ethylenically unsaturated monomer, for example methyl vinyl ether/maleic anhydride having a molecular weight (M.W.) of about 30,000 to about 1,000,000, most preferably about 30,000 to about 800,000, e.g., in amounts ranging from about 0.65 to about 3% by weight;

2.19. The foregoing plaque removal gel comprising one or more synthetic anionic polymeric polycarboxylates and further comprising an antibacterially effective amount of triclosan;

2.20. Any of the foregoing gels wherein the antiplaque agent comprises a chelating agent, e.g., selected from one or more a soluble pyrophosphates, for example alkali metal pyrophosphate salts, e.g., pyrophosphate, tripolyphosphate, hexametaphosphate, tetra alkali metal pyrophosphate, dialkali metal diacid pyrophosphate, trialkali metal monoacid pyrophosphate and mixtures thereof, wherein the alkali metal is sodium or potassium, e.g., in an amount of at least about 1.0 wt. % pyrophosphate ions, about 1.5 wt. % to about 6 wt. %, about 3.5 wt. % to about 6 wt. % of such ions.

The invention thus provides in one embodiment an oral care system (System 1) comprising
- a gel, e.g., a plaque indicator gel according to any of the preceding embodiments, e.g., Gel 1, et seq. and/or a plaque removal gel, e.g., Gel 2, et seq., contained in a dispenser, wherein
- the gel has a Herschel-Bulkley yield stress of 10 to 230 dynes/cm2, e.g., 30 to 45 dynes/cm2, a Herschel-Bulkley viscosity of 3 to 500 poise, e.g., 30 to 45 poise, and a Herschel-Bulkley rate index of 0.4 to 0.6, e.g. 0.5 to 0.6, and
- the dispenser (Dispenser 1) comprises: a housing having a longitudinal axis and an internal reservoir containing the gel; a dispensing orifice in the housing for dispensing the gel from the reservoir; a removable or displaceable cap which can cover the dispensing orifice when the dispenser is not in use; and means for dispensing the gel from the dispensing orifice;

for example the oral care system of System 1 comprising 1.1. Dispenser 1 wherein the means for dispensing the gel is a surface at the end of the internal reservoir which is distal to the dispensing orifice and axially movable towards the orifice, such that when the surface is moved towards the dispensing orifice, the gel is dispensed, for example wherein the surface is moved by means of external pressure or by means of a drive screw which exerts force to move the surface when the drive screw is turned;

1.2. A dispenser, e.g. according to 1 or 1.1 comprising a longitudinally elongated housing having a distal end with an applicator therein and an opposite proximal end; a reservoir disposed in the housing for holding a plaque indicator gel as hereinbefore described, the reservoir in fluid communication with the applicator;

1.3. Dispenser 1 or 1.1 comprising a collar within the housing, the collar comprising an axial passageway and a cam surface, the collar being non-rotatable with respect to the housing; a reciprocator comprising an actuator, a drive screw extending through the axial passageway of the collar, and a cam surface, the reciprocator being rotatable with respect to the housing; a resilient member that axially biases the cam surface of the reciprocator and the cam surface of the collar into mating contact; an elevator forming an end wall of the reservoir, the elevator being non-rotatable with respect to the housing and threadily coupled to the drive screw; and wherein rotation of the actuator causes the elevator to (1) axially advance along the drive screw in a first axial direction due to relative rotation between the drive screw and the elevator, and (2) axially reciprocate due to relative rotation between the cam surface of the collar and the cam surface of the reciprocator;

1.4. Any of the foregoing dispensers wherein the dispenser forms all or part of the handle of a toothbrush, for example wherein the head portion of the toothbrush forms the cap of the dispenser, or wherein the head portion of the toothbrush can be rotated to turn a drive screw which dispenses the gel from the opposite end;

1.5. Any of the foregoing dispensers wherein the dispensing orifice comprises a brush suitable for controlled application of the gel to the teeth;

1.6. Any of the foregoing dispensers wherein the dispensing orifice is in the form of a doe foot suitable for controlled application of the gel to the teeth;

1.7. Any of the foregoing dispensers wherein the exterior surface of the dispensing orifice comprises an elastomeric material;

1.8. Any of the foregoing dispensers wherein the exterior surface of the dispensing orifice has nubbins;

1.9. Any of the foregoing dispensers wherein the gel is dispensed as a shear rate of 50-200/s, e.g., 75-125/s, e.g., about 100/s;

1.10. Any of the foregoing dispensers comprising a plaque indicator gel, e.g., a gel according to Gel 1, et seq.

1.11. Any of the foregoing dispensers comprising a plaque removal gel, e.g., a gel according to Gel 2, et seq.

1.12. A kit or unit comprising a first dispenser and second dispenser, each according to any of the foregoing dispensers, the first dispenser providing a plaque indicator gel, e.g., according to Gel 1, et seq. and the second dispenser providing a plaque removal gel, e.g., according to Gel 2, et seq.

Examples of dispensers suitable for use in oral care systems according to the present invention include those more fully described, for example, in WO 2011/079028, WO/2011/078864, and WO/2011/078863, the contents of which are incorporated herein by reference. Particular embodiments include oral care systems utilizing dispensers having a reservoir and a dispensing orifice in the form of a brush or a doe foot, wherein the dispenser forms the handle of a toothbrush, for example where the head of the toothbrush is removed when the gel is dispensed or the head of the toothbrush is turned to dispense the gel from the opposite end.

In a further embodiment, the invention provides a method of detecting and removing plaque comprising applying a plaque indicator gel according to any of the preceding embodiments, e.g., Gel 1, et seq., in an oral care system comprising the gel in a dispenser, e.g. a dispenser according to Dispenser 1, et seq., to the teeth of a subject in need thereof, and brushing away the plaque revealed thereby; as well as the use of a plaque indicator gel according to any of the preceding embodiments, e.g., Gel 1, et seq., in such a method or in the manufacture of an oral care system for use in such a method.

In a further embodiment, the invention provides a method of removing plaque comprising first applying a plaque removal gel according to any of the preceding embodiments, e.g., Gel 2, et seq., in an oral care system comprising the gel in a dispenser, e.g. a dispenser according to Dispenser 1, et seq., to the teeth of a subject in need thereof, and then brushing the teeth; as well as the use of a plaque removal gel according to any of the preceding embodiments, e.g., Gel 2, et seq., in such a method or in the manufacture of an oral care system for use in such a method.

In a further embodiment, the invention provides a method of detecting and removing plaque comprising applying a plaque indicator gel according to any of the preceding embodiments, e.g., Gel 1, et seq., in an oral care system comprising the gel in a dispenser, e.g. a dispenser according to Dispenser 1, et seq., to the teeth of a subject in need thereof, then applying a plaque removal gel according to any of the preceding embodiments, e.g., Gel 2, et seq., optionally in an oral care system comprising the gel in a dispenser, e.g. a dispenser according to Dispenser 1, et seq., to the teeth where the plaque indicator gel indicates the presence of plaque, and then brushing the teeth; as well as the use of a plaque indicator gel according to any of the preceding embodiments, e.g., Gel 1, et seq., or a plaque removal gel according to any of the preceding embodiments, e.g., Gel 2, et seq., in such a method or in the manufacture of an oral care system for use in such a method.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Example 1—Gel Formulation Optimization

Different gel formulations are prepared and tested to determine suitability for administration with a pen-type dispenser. Many of the formulae tested are too runny or too thick for use with the pen dispenser. Three formulae identified as having potentially acceptable rheological properties based on the initial visual evaluation and testing with pen dispenser are selected for more detailed evaluation. Formulae A, B, and C are prepared in accordance with the following table (ingredients by weight % of total formula).

| Ingredient | A | B | C |
|---|---|---|---|
| Demineralized Water | 56.24 | 54.94 | 52.14 |
| Sodium Saccharin | 0.50 | 0.50 | 0.50 |
| Sodium Fluoride | 0.11 | 0.11 | 0.11 |
| 99.0%-101.0% Glycerin - USP Vegetable Source | 20.00 | 20.00 | 20.00 |
| Xanthan Gum | 0.20 | 0.50 | 1.50 |
| Sodium CMC - Type 7 | 0.20 | 1.20 | 3.00 |
| Sorbitol - Non-Browning/Crystal-NF 70% solution | 20.00 | 20.00 | 20.00 |
| Sodium Lauryl Sulfate Powder | 1.50 | 1.50 | 1.50 |
| Coolest Crystal Mint Flavor | 1.20 | 1.20 | 1.20 |
| FD&C Green No. 3 | 0.05 | 0.05 | 0.05 |

The formulae are compared for suitability in the intended use, testing the formulae in two different pen dispenser types, one with a doe foot tip and the other with a brush tip. The results are summarized in the following table:

| | A | B | C |
|---|---|---|---|
| Dispensing | Poor - runs off applicator | Acceptable | Product splits brush, unacceptable for doe foot - product keeps dispensing after turning applicator |
| Stand Up | Unacceptable - runs off applicator and brush | Acceptable - stays on applicator | Acceptable |
| Application | Unacceptable, runs upon application | Spreads evenly with all applicators | Unacceptable - Spreading is difficult with doe foot and brush |
| Plaque Disclosing | Acceptable | Acceptable | Unacceptable - Difficult to spread for effective plaque disclosing |

The composition of Formula B is seen to be the most suitable for this application. The critical differences between the three formulae relate to their rheological properties, as seen in the following summary table:

| Condition | Relevant Rheological Property |
|---|---|
| Dispensing | Viscosity profile G'/G" |
| Stand Up | Critical stress |
| Application | Viscosity at shear rate of ~1000 s$^{-1}$ |
| | Critical stress |
| Plaque Disclosing | Critical stress |

The selected gels are non-Newtonian, exhibiting non-linear shear-thinning properties at different levels of force. The specific rheological properties of the formulations are measured using an AR1000 rheometer from TA Instruments with the 4 cm 2 degree cone geometry. Viscoelastic properties, such as the elastic modulus (G') and the loss modulus (G"), are obtained from strain sweep experiments. For the strain sweep measurements, the angular frequency is held at 1 Hz while the strain is varied from 0.1 to 500%. Viscosity measurements are obtained from steady state flow experiments, which are conducted varying the shear rate from 1000 to 0.1 s$^{-1}$. The data is plotted into the Herschel-Bulkley (HB) Model (shear stress=yield stress+viscosity* (shear rate)$^{rate\ index}$):

| Formula | G' (dyne/cm$^2$) | G" (dyne/cm$^2$) | Critical Stress (dyne/cm$^2$) | G'/G" | HB fit: yield stress (dyne/cm$^2$) | HB fit: viscosity (poise) | HB fit: rate index |
|---|---|---|---|---|---|---|---|
| A | 22.66 | 17.61 | 2.151 | 1.286768881 | 8.628 | 2.429 | 0.6639 |
| B | 330 | 151.3 | 5.06 | 2.181097158 | 37.67 | 39.32 | 0.5342 |
| C | 2170 | 909.7 | 19.39 | 2.385401781 | 285.3 | 631.1 | 0.3754 |

Based on the suitability and rheological data, gels for this application should have (i) HB yield stress greater than Formula A and less than Formula C, e.g., about that of Formula B, (ii) HB viscosity greater than Formula A and less than Formula C, e.g., about that of Formula B, and (iii) HB rate index less than Formula A and greater than Formula C, e.g., about that of Formula B.

Example 2—User Testing

The composition of Formula B is then assessed by potential users for performance using a pen dispenser system. The purpose of this development is to use the plaque disclosing technology as a gel that could be conveyed through a more targeted delivery system. The more targeted delivery allows for a lower dye dose, overcoming the unacceptable messiness and user dissatisfaction seen in an earlier trial with plaque-disclosing toothpaste. The delivery system being explored in this test is a pen applicator with two different tips—a brush tip and a doe foot tip. The subjects use the pen applicators to apply the plaque-disclosing gel to their teeth, check for stained plaque, and then brush away the disclosing gel and plaque.

The purposes of the user study are to assess the plaque disclosing capability of the gel when applied using a pen applicator, assess if there are any issues with staining of soft tissue or plaque with the gel, and observe user interaction with the two pen applicators for targeted delivery, to uncover how they use the applicators, any issues with the system and if this system would change their brushing behavior.

The study is a sequential monadic (one prototype per day) central location test. Product presentation is unbranded. Randomization is not done across respondents as doe-foot applicator was not available the first Monday of fielding. Teeth and gums of every respondent are photographed after their usage of the plaque disclosing gel and pen applicators.

The thirty test participants visit the test facility on two consecutive Monday afternoons where they use one of the plaque disclosing prototypes and then brush their teeth with 1.0 g of toothpaste. Feedback on the process is collected using the Compusense direct data entry system. Photos capture the stained plaque on everyone's teeth after using each pen applicator with the plaque disclosing gel. Panelists are asked to refrain from brushing at least 24 hours prior to each of the test sessions. The mean ratings and frequency distribution are reported for each question at 90% confidence level.

Some comments by subjects on their experiences using both pen applicators:

"Showed plaque better than expected"

"Was easy to apply, spread well and gel has a fresh minty taste"

"Thought it would be worse for flavor and time, wasn't expecting a pleasant experience"

100% of subjects report that plaque on their teeth is revealed, regardless of whether they use the brush tip or doe foot tip applicator. More than 80% of the subjects find it extremely easy to very easy to remove the stained plaque during brushing after using either the brush tip or doe foot tip applicator. Following brushing, there is little to no color remaining on their teeth, lips or cheeks and no color remaining on their gums. Most subjects do not perceive either of the two applicators as being messy during use. Less than 10% of subjects express dissatisfaction with the products. Several subjects comment that the product would change their brushing habits by indicating areas where they need to brush more and to pay more attention to problem areas (greater stain), and also that product would be great for children, inducing them to brush longer and more carefully.

This feedback from actual product use confirms that this product has substantial advantages over the existing products and is effective to provide efficient and effective plaque disclosure. The feedback is very positive compared to a prior trial using a plaque-revealing dentifrice, which the subjects view as messy and unappealing.

The invention claimed is:

1. An oral care system comprising a gel in a pen dispenser, the dispenser comprising a chamber which permits dispensing of a measured amount of the gel, wherein the gel exhibits a Herschel-Bulkley yield stress of 30 to 45 dynes/cm$^2$, a Herschel-Bulkley viscosity of 30 to 45 poise, and a Herschel-Bulkley rate index of 0.5 to 0.6, and wherein the gel comprises 0.2-1.5% xanthan gum, 1-2% carboxymethyl cellulose, 30-50% humectants selected from glycerin, sorbitol, xylitol, and combinations thereof, and 50-60% water.

2. The oral care system of claim 1 wherein the dispenser comprises a housing having a longitudinal axis and an internal reservoir containing the gel; a dispensing orifice in the housing for dispensing the gel from the reservoir; a removable or displaceable cap which can cover the dispensing orifice when the dispenser is not in use; and means for dispensing the gel from the dispensing orifice.

3. The oral care system of claim 2 wherein the means for dispensing the gel is a surface at the end of the internal reservoir which is distal to the dispensing orifice and axially movable towards the orifice, such that when the surface is moved towards the dispensing orifice, the gel is dispensed.

4. The oral care system of claim 3 comprising a collar within the housing, the collar comprising an axial passageway and a cam surface, the collar being non-rotatable with respect to the housing; a reciprocator comprising an actuator, a drive screw extending through the axial passageway of the collar, and a cam surface, the reciprocator being rotatable with respect to the housing; a resilient member that axially biases the cam surface of the reciprocator and the cam surface of the collar into mating contact; an elevator forming an end wall of the reservoir, the elevator being non-rotatable with respect to the housing and threadily coupled to the drive screw; and wherein rotation of the actuator causes the elevator to (1) axially advance along the drive screw in a first axial direction due to relative rotation between the drive screw and the elevator, and (2) axially reciprocate due to relative rotation between the cam surface of the collar and the cam surface of the reciprocator.

5. The oral care system according to claim 1 wherein the dispenser forms all or part of the handle of a toothbrush.

6. The oral care system according to claim 1 wherein the dispenser comprises a plaque indicator gel comprising a dye.

7. The oral care system according to claim 1 wherein the dispenser comprises a plaque removal gel comprising an antiplaque agent.

8. The oral care system according to claim 1 comprising
a) A first dispenser comprising a plaque indicator gel comprising a dye, and
b) A second dispenser comprising a plaque removal gel comprising an antiplaque agent.

9. The oral care system according to claim 1 wherein the elastic modulus (G') of the gel is 200 to 500 dyne/cm$^2$ and the viscous modulus (G") of the gel is 100-300 dyne/cm$^2$.

10. The oral care system according to claim 1 wherein the gel comprises the following ingredients by weight percent:

| | |
|---|---|
| water | 50-60% |
| xanthan gum | 0.2-1.5% |
| sodium carboxymethylcellulose (CMC) | 1-2% |
| sorbitol (70% aqueous solution) | 15-25% |
| glycerin | 15-25% | active agent selected from
- dye in an amount effective to reveal plaque;
- antiplaque agent in an amount effective to remove plaque; and
- combinations thereof.

11. The oral care system according to claim 1 wherein the gel comprises flavorings selected from saccharin, mint flavor, and combinations thereof; a surfactant and a fluoride ion source.

12. The oral care system according to claim 10 wherein the gel comprises a dye selected from FD&C Red No. 3, FD&C Blue No. 1, FD&C Violet No. 1, FD&C Green No. 1, FD&C Green No. 2, FD&C Green No. 3, and mixtures thereof, in an amount effective to reveal plaque upon application.

13. The oral care system of claim 12 wherein the amount of dye is less than 0.1% by weight of the total gel formulation.

14. The oral care system according to claim 1 wherein the gel comprises an antiplaque agent selected from antibacterial agents and chelating agents in an amount effective to remove or inhibit plaque.

15. The oral care system of claim 14 wherein the antiplaque agent comprises triclosan.

16. A method of detecting and removing plaque comprising applying a plaque indicator gel using an oral care system of claim 1 to the teeth of a subject in need thereof, and brushing away the plaque revealed thereby.

17. A method of detecting and removing plaque comprising applying a plaque indicator gel using an oral care system of claim 1 to the teeth of a subject in need thereof, then applying a plaque removal gel using an oral care system in accordance with claim 1 to the teeth in places where the plaque indicator gel indicates the presence of plaque, and then brushing the teeth.

18. The oral care system of claim 1 wherein the gel comprises about 0.5% xanthan gum.

* * * * *